United States Patent
Randall et al.

(10) Patent No.: US 6,824,536 B2
(45) Date of Patent: Nov. 30, 2004

(54) SUBSTANTIALLY SERPENTINE SHAPED TAMPON

(75) Inventors: Catherine Jean Randall, Cincinnati, OH (US); Charles John Berg, Jr., Wyoming, OH (US); Andrea Kollwitz, Geneva (CH); Angela Alexa Schäfer, Schwalbach (DE); Rachel Ann Lawton, Frankfort (DE); Nanda Christine Almond, Walton, KY (US); Wolfgang Werner Hans Domeier, Kreuzau-Drove (DE); Sybille Fuchs, Frankfurt (DE)

(73) Assignee: The Procter & Gamble Company, Cincinnati, OH (US)

(*) Notice: Subject to any disclaimer, the term of this patent is extended or adjusted under 35 U.S.C. 154(b) by 309 days.

(21) Appl. No.: 10/150,050

(22) Filed: May 16, 2002

(65) Prior Publication Data

US 2003/0176844 A1 Sep. 18, 2003

Related U.S. Application Data

(60) Provisional application No. 60/365,426, filed on Mar. 18, 2002.

(51) Int. Cl.[7] .............................................. A61F 13/20
(52) U.S. Cl. ........................... 604/385.18; 604/385.17; 604/904; 604/385.01
(58) Field of Search ....................... 604/385.17, 385.18, 604/385.01, 904, 540, 11–14, 954

(56) References Cited

U.S. PATENT DOCUMENTS

| 2,123,750 | A | | 7/1938 | Schulz |
| 3,572,341 | A | * | 3/1971 | Glassman .................... 604/359 |
| 3,738,364 | A | | 6/1973 | Brien et al. |
| 3,854,481 | A | | 12/1974 | Messing |
| 3,946,737 | A | | 3/1976 | Kobler |
| 5,342,331 | A | * | 8/1994 | Silber et al. ................ 604/330 |
| 5,350,371 | A | | 9/1994 | Van Iten |
| 5,397,312 | A | * | 3/1995 | Rademaker et al. ........ 604/218 |
| 5,891,081 | A | | 4/1999 | McNelis et al. |
| 5,911,712 | A | | 6/1999 | Leutwyler et al. |
| 6,045,526 | A | * | 4/2000 | Jackson ....................... 604/15 |
| 6,071,259 | A | | 6/2000 | Steiger et al. |
| 6,283,952 | B1 | * | 9/2001 | Child et al. ................. 604/540 |
| 6,310,269 | B1 | | 10/2001 | Friese et al. |

* cited by examiner

*Primary Examiner*—John J. Calvert
*Assistant Examiner*—Jacqueline F Stephens
(74) *Attorney, Agent, or Firm*—Ingrid N. Hickman; Kevin C. Johnson

(57) ABSTRACT

Shaped tampons having varying volumes are provided. A tampon which is formed into a self-sustaining shape has an outer surface, which is substantially serpentine. The tampon also has continually changing volume. The shaped tampons may also have varying average fiber density regions. The shaped tampons may be wrapped in tightly conforming wrappers which optionally aid in maintaining the self-sustaining shape prior to use. Optionally, the shaped tampons may utilize tampon applicators which enable a user to visually see the shape of the tampon prior to use.

20 Claims, 4 Drawing Sheets

SUBSTANTIALLY SERPENTINE SHAPED TAMPON

This application claims the benefit of Provisional Application No. 60/365,426 filed on Mar. 18, 2002.

FIELD OF THE INVENTION

This invention relates to shaped absorbent tampons having varying volumes along the X axis of the tampon. The invention also relates to tightly conforming wrappers and to tampon applicators useful with the shaped absorbent tampons of the present invention.

BACKGROUND OF THE INVENTION

A wide variety of absorbent catamenial tampons have long been known in the art. Most commercially available tampons are substantially cylindrical in shape prior to use in order to facilitate vaginal insertion. It is well known that the vaginal canal is not smooth and linear, but rather is very contoured. Some tampons have tapered insertion ends to make insertion more comfortable. Others have flared withdrawal ends, perhaps to provide a larger surface area for the user to push against during insertion. Nevertheless, the inventors of the present invention have learned that comfort and/or ease of the insertion of tampons is an important unmet consumer need. It is also important to have a tampon which is comfortable once inside the contoured vaginal canal. Additionally, it is desirable that the features rendering a tampon comfortable and/or easy to insert do not compromise, and alternatively even enhance the fluid acquisition capabilities of the tampon in use.

The present invention provides comfortable shaped tampons. The shaped tampons aid in the insertion ease and/or comfort. The tampons of the present invention may optionally have varying density regions to further facilitate insertion ease and/or comfort while enhancing fluid acquisition into the tampon.

SUMMARY OF THE INVENTION

This invention relates to shaped tampons having varying volumes. A tampon is formed into a self-sustaining shape having an outer surface, which is substantially serpentine. The tampon also has continually changing volume. The shaped tampons may also have varying average fiber density regions. The tampons of the present invention may optionally include tightly conforming wrappers which may aid in maintaining the tampon's self-sustaining shape prior to use. The tampons may also optionally utilize tampon applicators which allow the user to visualize the shape of the tampon prior to use.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

Figure 1:
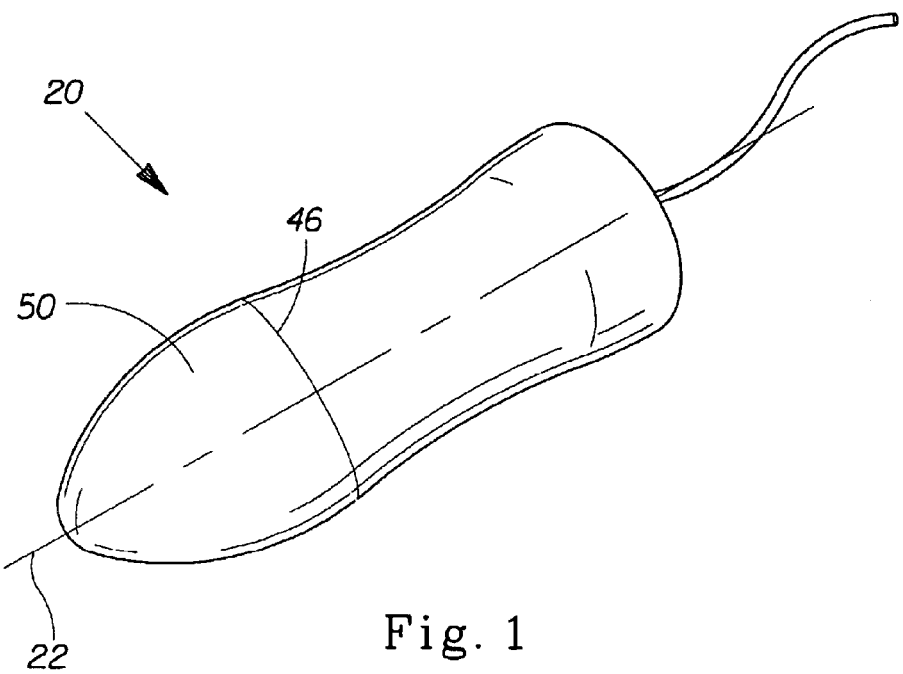
FIG. 1 is perspective view of outer surface of a shaped tampon

The present invention is directed to a shaped tampon. The Figures show various embodiments of such a shaped tampon 20. The present invention, however, is not limited to a structure having the particular configurations shown in the drawings.

The term "tampon" refers to any type of absorbent structure which is inserted into the vaginal canal or other body cavities for the absorption of fluid therefrom. The "outer surface" of a tampon refers to the visible surface of the (compressed and/or shaped) tampon prior to use and/or expansion. The outer surface may optionally be aesthetically textured, such as with ribs, spiraling ribs, a mesh pattern, etc. Typically, tampons are constructed from an absorbent material, which has been compressed and/or shaped in any or all of the width direction, the radial direction, and the axial direction, in order to provide a tampon which is of a size and stability to allow insertion within the vagina or other body cavity. A tampon has a "self-sustaining shape" when a tampon pledget has been compressed and/or shaped such that it assumes a general shape and size, which is vaginally insertable, absent external forces. It will be understood by one of skill in the art that this self-sustaining shape need not, and preferably does not persist during actual use of the tampon. That is, once the tampon is inserted and begins to acquire fluid, the tampon may begin to expand and may lose its self-sustaining form.

As used herein the terms "pledget" or "tampon pledget" are intended to be interchangeable and refer to a construction of absorbent material prior to the compression of such construction into a tampon as described above. Tampon pledgets are sometimes referred to as a tampon blank, or a softwind, and the term "pledget" is intended to include such terms as well. In general in this specification, the term "tampon" is used to refer to a finished tampon after the compression and/or shaping process. It will be recognized by those of skill in the art that in some contexts these terms are interchangeable. The different stages of tampon manufacture are described herein with an eye toward providing the greatest possible clarity. Therefore, the terms used are to assist the reader in best understanding the features of the invention and not to introduce limitations in the terms not consistent with the context in which they are used in this specification.

As used herein the terms "vaginal cavity", "within the vagina", and "vaginal canal" are intended to be synonymous and refer to the internal genitalia of the human female in the pudendal region of the body. The term "vaginal canal" is intended to refer to the space located between the introitus of the vagina (sometimes referred to as the sphincter of the vagina) and the cervix and is not intended to include the interlabial space, including the floor of vestibule. The externally visible genitalia generally are not included within the term "vaginal canal" as used herein.

The term "digital tampon" refers to a tampon which is intended to be inserted into the vaginal canal with the user's finger and without the aid of an applicator. Thus, digital tampons are typically visible to the consumer prior to use rather than being housed in an applicator.

Figure 2:
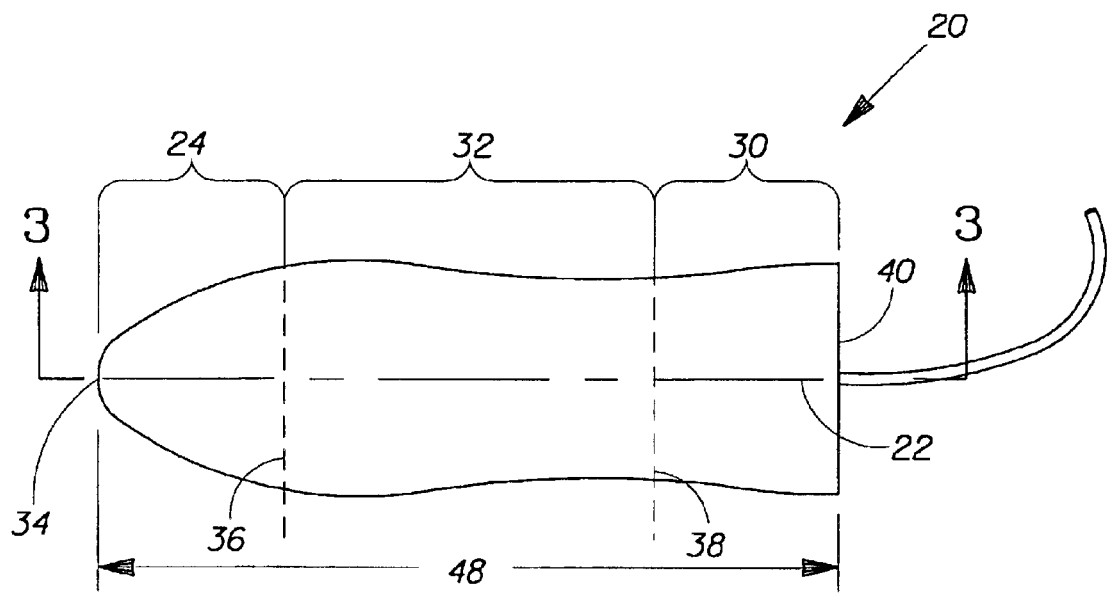
FIG. 2 is plan view of a shaped tampon showing the insertion end, withdrawal end, center region, and total length of the tampon.

The "X axis" of a tampon is the axis which runs longitudinally through the center of the tampon as shown in FIG. 2. A portion of the tampon may be asymmetric about the X axis, such as when a withdrawal end is flared and distorted from the original shape of the rest of the tampon (such as a "fin shape"). Further, the X axis may be linear or non-linear. The "perimeter" of a segment of the tampon is a distance measured around the outer surface of the tampon perpendicular to the X axis. The perimeter may be measured, for instance, using Resin Embedded Microtome along with Scanning Electron Microscopy—S.E.M. (supplied by companies such as Resolution Sciences Corporation; Corte Madera, Calif.). A "perimeter line" is created by the intersection with the outer surface of the tampon of a cross-section plane drawn perpendicular to the X axis. The perimeter is the length of this perimeter line. In cases where the X axis is non-linear, the cross-section plane is drawn perpendicular to a line tangent the X axis at the point of interest.

Tampons having "continually changing volume" are those where sequential segments of the tampon, taken along the X axis, have different volumes. For purposes of determining whether or not a tampon has constantly changing volumes herein, the volume of slices of tampons taken every 5 mm along the X axis may be compared. Such measurements can be determined using Resin Embedded Microtome along with Scanning Electron Microscopy—S.E.M. (supplied by companies such as Resolution Sciences Corporation; Corte Madera, Calif.).

The phrase "substantially serpentine" refers to a non-linear dimension between any two points spaced at least about 5 mm apart. The outer surface of the tampon is "substantially serpentine" when a "substantially serpentine line" is formed by the intersection of the outer surface with a plane passing through the X axis of a tampon. In other words, if the line formed from this intersection contains no portion greater than about 5 mm long which is linear, it is said to be "substantially serpentine".

The "inflection point" of an outer surface is the position on the outer surface that denotes a change in slope concave upward from one concave downward and vice versa.

The term "insertion edge" refers to the plane containing the absolute end of the insertion end. The phrase "insertion end" refers to the end of the tampon, beginning with the insertion edge, which is intended to lead insertion of the tampon into the vagina. The insertion end begins at the insertion edge and ends at the "first transition position" which is the position at ¼ the total length of the self-sustaining shape down the X axis from the insertion edge. Thus, the total length of the insertion end is ¼ the total length of the self-sustaining shape.

The term "center region" refers to the portion of the tampon located between the insertion end and the withdrawal end. The center region begins at the first transition position. The center region ends at a "second transition position", which is the position at ¾ the total length of the self-sustaining shape down the X axis from the insertion edge. Thus, the length of the center region is ½ the total length of the tampon.

The term "withdrawal edge" refers to the plane containing the absolute end of the withdrawal. The phrase "withdrawal end" refers to the end of the tampon opposite the insertion end, which begins with the withdrawal edge. The withdrawal end begins at the second transition position. The withdrawal end terminates at the withdrawal edge. Thus, the length of the withdrawal end is ¼ of the total length of the tampon.

The term "largest insertion end perimeter" refers to the largest perimeter within the insertion end, excluding the perimeter at the first transition position. The term "smallest withdrawal end perimeter" refers to the smallest perimeter within the withdrawal end, excluding the perimeter at the second transition position.

The "total length of the tampon" refers to the length of the X axis of the tampon beginning at the insertion edge and ending at the withdrawal edge. Thus, the total length of the tampon does not include the length of any overwrap, secondary absorbent member or withdrawal cord which extends beyond the main absorbent material ending at the withdrawal edge.

The term "tapered" refers to a gradually narrowing portion of a tampon. An insertion end is "tapered" when the insertion end or a portion thereof has a plurality of gradually decreasing perimeters approaching the insertion edge. The term "flared" refers to a widening portion of a tampon. A withdrawal end is "flared" when the withdrawal end or a portion thereof has a plurality of gradually increasing perimeters approaching the withdrawal edge.

The "average fiber density" of a region, refers to the average fiber density of the fibers in the region. The average fiber density may be measured using Micro Cat Scan or Resin Embedded Microtome along with Scanning Electron Microscopy—S.E.M. (supplied by companies such as Resolution Sciences Corporation; Corte Madera, Calif.).

The phrase "maximum perimeter region" refers to a region on the tampon measuring 5 mm on either side of the largest perimeter of the insertion end and the center region. Thus, the maximum perimeter region is a region that is 10 mm long. The phrase "minimum perimeter region" refers to a region on the tampon measuring 5 mm on either side of the smallest perimeter of the center region and the withdrawal end, excluding the withdrawal edge. Thus, the minimum perimeter region is a region that is 10 mm long.

The abbreviation "g/cm$^2$" is "grams per square centimeter". The abbreviation "mm" is millimeter. The abbreviation mm$^3$ is cubic millimeters.

FIG. 1 shows a perspective view of one embodiment of the shaped tampon 20 of the present invention. The tampon has an X axis 22 that runs lengthwise through the tampon. The outer surface 50 of the tampon is shown.

FIG. 2 is a plan view of one embodiment of the shaped tampon of the present invention. The tampon 20 has a total length 48 and is a mass of absorbent material compressed into a self-sustaining shape comprising a substantially serpentine outer surface. The tampon has an X axis 22 that runs lengthwise through the tampon. The tampon 20 has an insertion end 24, a withdrawal end 30, and a center region 32 that is located between the insertion end 24 and the withdrawal end 30. The insertion end 24 begins with and insertion edge 34 and ends at the first transition position 36, which is the point at ¼ of the self sustaining shape down the X axis 22 from the insertion edge 34. The center region begins at the first transition position 36 and ends at the second transition position 38. The withdrawal end 30 is opposed to the insertion end 24 and begins at the second transition position 38 and terminates at the withdrawal edge 40. The withdrawal end is ¼ of the total length of the tampon 20.

Figure 3:
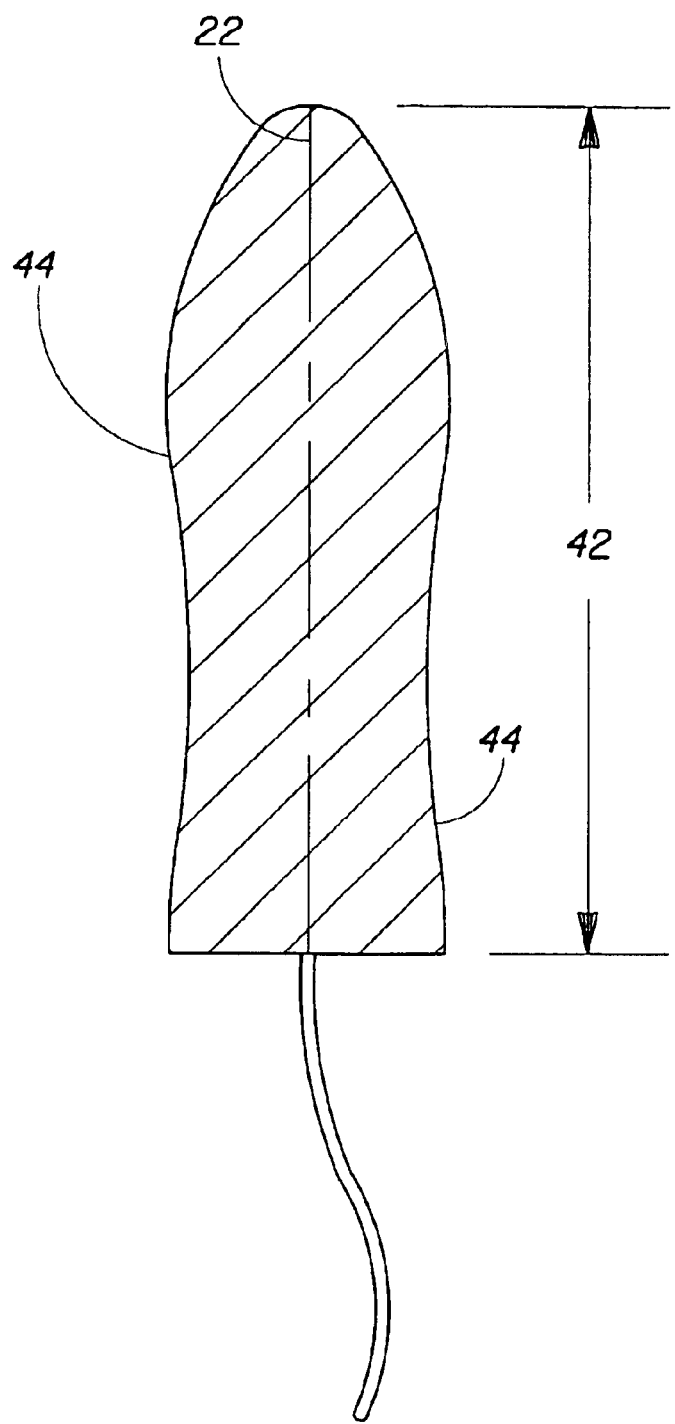
FIG. 3 is a lengthwise cross-section along the X axis showing the substantially serpentine line and inflection point.

FIG. 3 is a lengthwise cross-section along the X axis showing the substantially serpentine line 42 and inflection point 44. The substantially serpentine line is formed by the intersection of the outer surface with a plane passing through the X axis of the tampon.

Figure 4:
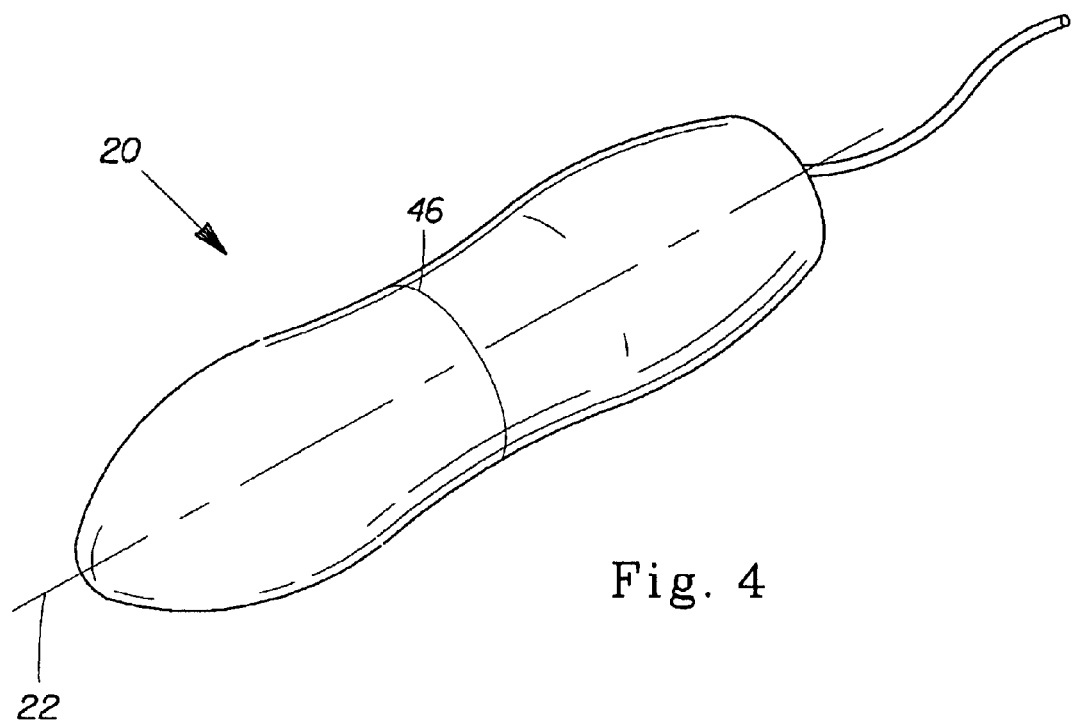
FIG. 4 is a perspective view of one embodiment of the shaped tampon present invention showing a perimeter line.

FIG. 4 is a perspective view of one embodiment of the shaped tampon 20 of the present invention showing the perimeter line 46. The shaped tampon has continually changing volumes. In this embodiment, the perimeter in the center region is less than both a largest insertion end perimeter and smallest withdrawal end perimeter.

Figure 5:
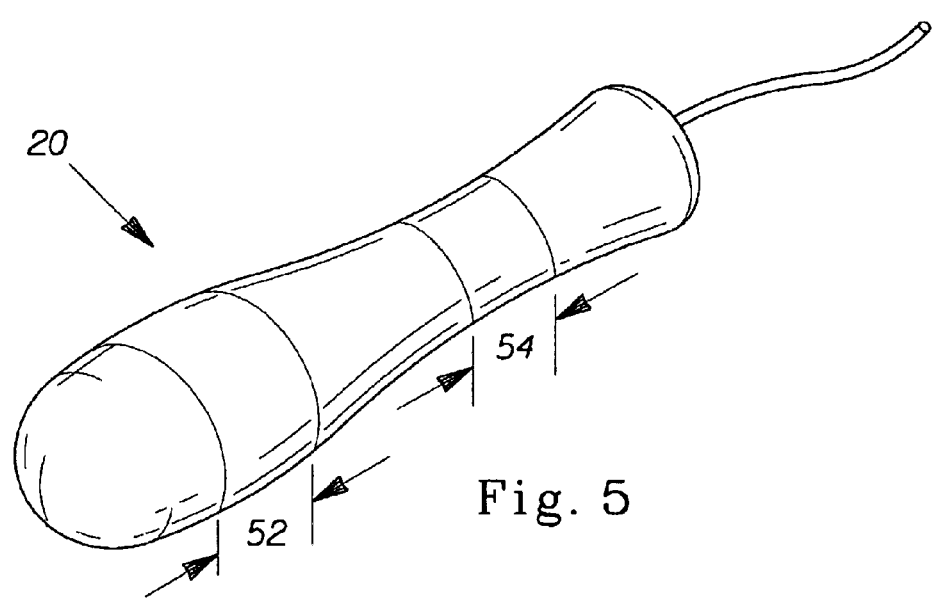
FIG. 5 is perspective view of alternative embodiment of the shaped tampon showing a perimeter line.

FIG. 5 shows an alternative embodiment of the shaped tampon 20 of the present invention. The tampon 20 has a maximum perimeter region 52 and minimum perimeter region 54. Both the maximum perimeter 52 region and minimum perimeter region 54 are 10 mm long. In this embodiment, the perimeter in the center region that is less than both a largest insertion end perimeter and the smallest withdrawal end perimeter.

Figure 6:
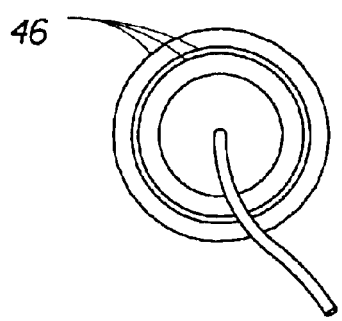
FIG. 6 is an end view of the embodiment shown in FIG. 5 showing multiple perimeter lines.

FIG. 6 is an end view from the withdrawal end of the embodiment shown in FIG. 5 showing multiple perimeter lines 46.

Figure 7:
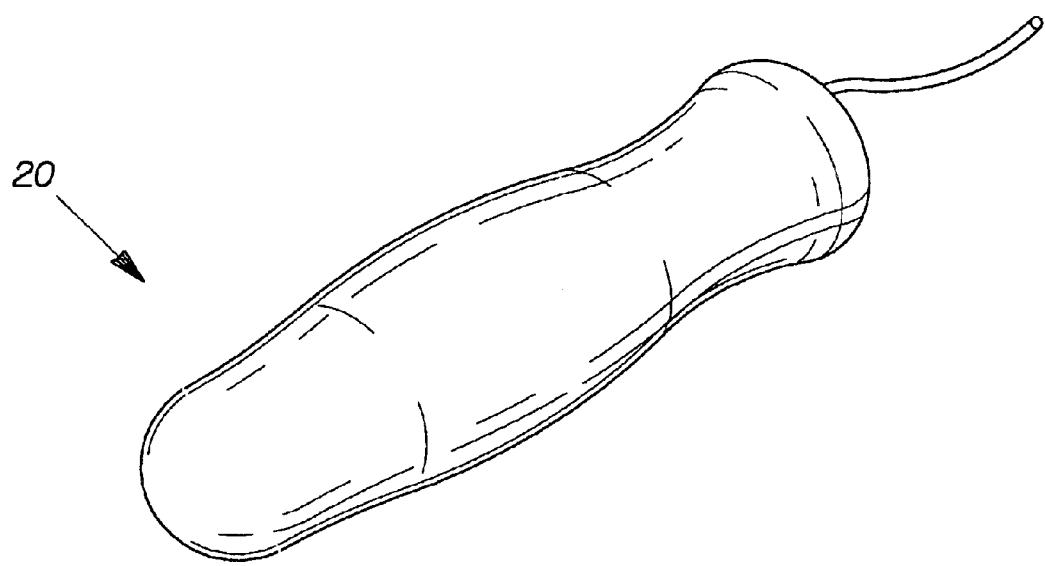
FIG. 7 is a perspective view of an alternative embodiment of the shaped tampon showing a perimeter line.

FIG. 7 is a perspective view of an alternative embodiment of the shaped tampon 20. In this embodiment, the perimeter in the center region is greater than both a largest insertion end perimeter and the smallest withdrawal end perimeter. The tampon has an X axis 22 that runs lengthwise through the tampon.

I. Shaped Tampons of the Present Invention

In order to better understand the present invention, a detailed description of several preferred embodiments is given. This description is intended to be by way of example, and not to limit the invention to these preferred embodiments. One of ordinary skill in the art will appreciate from this description how to make and use tampons incorporating the various features of the present invention although not every conventional feature is described in undue detail. The tampons of the present invention comprise a mass of absorbent material compressed into a self-sustaining shape which comprises a withdrawal end, a center region, and an insertion end.

The insertion ends and withdrawal ends of the tampons of the present invention may be entirely or partially flared or tapered. In one embodiment, at least a portion of the withdrawal end of a tampon according to the present invention is flared, beginning for instance at the second transition position. In the case where the entire withdrawal end is flared, the withdrawal edge would have a larger perimeter than the second transition position. Optionally, only a portion of the withdrawal end could be flared, followed by a tapered portion which terminates at the withdrawal edge. In this case the withdrawal end will have a perimeter which is greater than the withdrawal edge perimeter. In this case, the perimeter increases and then decreases between the second transition position and the withdrawal edge. In another embodiment, at least a portion of the insertion end is tapered, terminating with a smallest perimeter of the insertion end at the insertion edge.

A. Outer Surfaces which are Substantially Serpentine and Define Continually Changing Volumes:

The present invention relates to tampons which comprise a self-sustaining shape having an outer surface which define continually changing volumes along the X axis. These tampons further have an outer surface which is substantially serpentine. For example, the continually changing volumes may comprise a series of 5 mm regions having increasing volumes followed by a series of 5 mm regions having decreasing volumes, followed by another series of 5 mm regions having a series of increasing volumes. Alternatively, the continually changing volumes may comprise a series of 5 mm regions having decreasing volumes followed by a series of 5 mm regions having increasing volumes, followed by another series of 5 mm regions having a series of decreasing volumes. It should be understood that a tampon is considered to have continually changing volumes despite the possibility that 2 sequential 5 mm regions have the same volume. For instance, this may occur where the 2 sequential 5 mm regions divide a symmetrically shaped bulb or waist region equally. Each of the above particular embodiments defines at least one inflection point on the substantially serpentine line. Other embodiments further comprising additional series of increasing and/or decreasing volumes are also envisioned, which result in at least two inflection points on the substantially serpentine line.

In addition to having an outer surface which defines continually changing volumes and is substantially serpentine, certain embodiments may optionally have perimeter restrictions such as those described below in section B. In yet another embodiment, the center region may have a perimeter which is greater than or equal to all other perimeters, as shown in FIG. 7.

B. Embodiments Comparing the Perimeters of Center Regions to the Insertion End and Withdrawal End Perimeters:

Tampons of the present invention may optionally also have at least one perimeter in the center region which is less than the largest insertion end perimeter and/or a withdrawal end perimeter. Thus, embodiments fitting this description may have at least one "waist" or narrowing point in the center region as compared to the withdrawal end and the insertion end, which can readily be seen, for example, in FIGS. 1–5. Another embodiment includes a tampon where the center region has at least one perimeter which is less than all withdrawal end perimeters, such as when the entire withdrawal end is flared as in FIG. 2.

Embodiments included within this description also include, but are not limited to tampons wherein at least one of the center region perimeters is from about 5% to about 25%, alternatively from about 10% to about 15% smaller than the largest insertion end perimeter. Similarly, at least one of the center region perimeters may be from about 5% to about 25%, alternatively from about 10% to about 15% smaller than the largest withdrawal end perimeter.

C. Density Changes Along the X Axis:

It may be desirable to have fiber density changes along the X axis in some embodiments of the present invention. Such density changes may increase comfort and fluid acquisition. Such density changes may apply to all shaped tampons of the present invention described above. In particular, it may be desirable to have the average fiber density of the withdrawal region less than the average fiber density of the minimum perimeter region, which is often, but not necessarily located at a "waist" of the center region discussed above. Similarly, it may be desirable to have the average fiber density of the maximum perimeter region, which typically resembles a bulb near the insertion end of the center region, which is less than the average fiber density of the minimum perimeter region. Such constructions can not only increase comfort and insertion ease, but also provides a fluid acquisition benefit since the lower average fiber density regions can absorb fluid quickly and move it to the higher average fiber density region for storage.

While it is envisioned that a tampon can be constructed according to the present invention to have uniform or any combination of average fiber density changes, some examples of the varying density embodiments described above include but are not limited to tampons which have a minimum perimeter region average fiber density that is from about 105% to about 150%, alternatively from about 110% to about 130% of the maximum perimeter region average fiber density. Alternatively, or additionally, the tampons may have a minimum perimeter region average fiber density that is from about 105% to about 150%, alternatively from about 110% to about 130% of the withdrawal end average fiber density.

Varying average fiber density regions can be achieved through a variety of approaches when dealing with the shaped tampons of the present invention. For instance, the desired density changes may occur naturally when shaping a pledget into the shaped tampons of the present invention. Alternately, the tampon pledget may itself have a density profile tailored to provide the desired average fiber density regions upon compression and/or shaping. For example, a web may comprise low average fiber density rayon in an area near the edges of the web, which become at least a portion of the insertion end and/or the withdrawal end, and a higher average fiber density cotton/rayon blend in the center of the web such that when properly registered, the desired average fiber density regions result.

Another approach is to start with different shaped tampon pledgets, resulting in varying amounts of starting material in different regions prior to compression. Useful shapes for pledgets when using this approach include but are not limited to "softened rectangles" having curved sides, chevron shapes, or a shape resembling an open book.

When tampons of the present invention are created by rolling the pledget prior to compression and/or shaping, a portion of the absorbent material can be displaced from the withdrawal end to the insertion end as described in U.S. Pat. No. 6,283,952. Alternatively, a tapered compression rod used at the withdrawal end may be used to displace material towards the center region regardless of the tampon construction.

The selection of which method(s) to employ to achieve the desired average fiber density variations described above will depend variables such as the tampon construction and processing restrictions, the absorbent material used and the desired final tampon absorbency, and the particulars of the desired shape. One of ordinary skill in the art will easily recognize how to employ these approaches individually or in combination to create the final desired product to provide the identified consumer benefits discussed above.

D. Tampon Materials and Components:

The pledget may be constructed from a wide variety of liquid-absorbing materials commonly used in absorbent articles. Such materials include but are not limited to rayon (such as GALAXY Rayon (a tri-lobed rayon structure) available as 6140 Rayon; or SARILLE L rayon (a round fiber rayon), both available from Acordis Fibers Ltd., of Hollywall, England), cotton, folded tissues, woven materials, nonwoven webs, synthetic and/or natural fibers or sheeting, comminuted wood pulp which is generally referred to as airfelt, or combinations of these materials. Additionally, superabsorbent materials, such as superabsorbent polymers or absorbent gelling materials may be incorporated into the tampon.

The pledget can be rectangular or any other shape prior to compression and/or shaping. A more detailed description of liquid-absorbing materials and pledget shapes and dimensions can be found in co-pending case Ser. No. 10/039,979, filed Oct. 24, 2001, entitled "Improved Protection and Comfort Tampon", to Agyapong et al., Docket Number 8758.

The tampon of the present invention optionally includes a withdrawal cord, a secondary absorbent member, a liquid permeable overwrap material, and/or an applicator. Withdrawal cords useful in the present invention may be made of any suitable material known in the prior art and include cotton and rayon. Additionally, the tampons of the present invention may also benefit from a secondary absorbent member. U.S. Pat. No. 6,258,075 to Taylor et al. entitled "Tampon with Enhanced Leakage Protection" describes tampons having a variety of secondary absorbent members in great detail. Optional overwrap materials useful herein include rayon, cotton, bicomponent fibers, polyethylene, polypropylene, other suitable natural or synthetic fibers known in the art, and mixtures thereof.

The tampons of the present invention are typically inserted digitally. When the tampons are intended to be digitally inserted, it may be desirable to provide a finger indent at the withdrawal end of the tampon to aid in insertion. A finger indent can be made using a compression rod. An example of finger indents is found in U.S. Pat. No. 6,283,952, filed May 5, 1997, entitled "Shaped Tampon".

II. Optional Applicators Useful with the Shaped Tampons of the Present Invention Alternatively, the insertion may be aided through the use of any applicator adapted from the prior art for use with the shaped tampon. Prior art applicators of typically a "tube and plunger" type arrangement may be plastic, paper, or other suitable material. Additionally, a "compact" type applicator is also suitable. Since shaped tampons offer an additional consumer benefit of aesthetic appeal, it is often desirable to combine the shaped tampon with an applicator type which enables the user to observe at least a portion or the whole shape of the shaped tampon. Two techniques which allow the user to better notice the shape of the tampon are to either make visual observation possible through the use of a translucent or even transparent applicator materials, or to provide a tampon applicator insertion end that better follows and hence better displays the profiled shape of the enclosed shaped tampon than the typical commercial tampon applicators comprising straight-walled cylindrical inserter tubes often made from molded plastic or laminated cardboard tubes. As used hereinafter, the phrase "translucent" is meant to include completely transparent materials as well as those having a lesser degree of transparency, yet allow for the user to see through the material to a degree sufficient to ascertain at least a portion of the shape of the tampon even in the absence of conforming the applicator shape to the profiled shape of the tampon. Optionally, an applicator may employ both techniques, allowing the user to see the shaped tampon prior to use through a translucent applicator which also conforms to the profiled shape of the enclosed tampon.

To provide for visual observation, it is desirable to select a material that will permit at least some degree of light transmission rendering at least a portion of the applicator, which partially or fully encloses the tampon, translucent. While a fuller light transmission may be desirable at times, an option is to tint the insertion end of the applicator to provide a colored view of the shaped tampon. Materials particularly well-suited include polymer resins such as polyethylene, polypropylene, polyester, cellophane, polyamide, poly(vinyl chloride), ethylene-vinyl acetate copolymer, polycarbonate, PET (poly(ethylene terephthalate)), and the like. Depending on the structural form of the insertion end of the applicator to be manufactured, particular polymers may be better suited for one form over another such as for injection molded versus film sheath insertion ends.

In order to provide for at least a degree of profiled shape observation along at least a portion of the applicator's insertion end, at least a portion of the insertion end should itself be shaped to a similar degree as the shaped tampon or even contact and conform to at least a portion of the surface of the shaped tampon. Rigid insertion end structures could be shaped in a suitable manner (e.g. by injection molding) to provide at least a degree of profiled shape observation. Alternatively, insertion ends of applicators made from flexible or pliable materials, such as films, paper and flexible wovens or non-wovens, can also be used. Such flexible or pliable insertion ends include those which partially or fully enclose the tampon comprising a "sleeve" or a "tube" (as in U.S. Pat. Nos. 2,922,422 and 2,922,423); a "sheath" (as in U.S. Pat. Nos. 2,092,427 and 3,749,093); a "barrel" (as in U.S. Pat. No. 5,135,475); a "bag" (as in U.S. Pat. No. 3,358,686); or a "film enclosure" (as in U.S. Pat. No. 4,610,659). When modifying these types of applicators and/or flexible insertion ends such that they conform to the outer surface of the shaped tampon, it often is helpful that the insertion end material has a thickness of less than about 1 mm.

One embodiment of an applicator comprising a sheath-type flexible insertion end is a telescoping cardboard applicator comprising a film cap for covering at least the insertion end of the tampon, a ring tube unit for holding at least a portion of the tampon, and a pusher tube for pushing on the withdrawal end of the tampon thereby expelling it from the ring tube unit, through the film cap. Alternatively, the user's finger may substitute as the pusher tube. The ring tube unit houses at least the withdrawal end portion of the shaped tampon and acts as a guide for the pusher tube. The film cap covers at least the insertion end of the tampon, optionally continuing partway down the sides of the shaped tampon, and is attached to the ring tube unit. For instance, the ring tube unit may be 35 mm long and have an internal diameter of 15 mm. The pusher tube may have a length of 73 mm and can fit inside the ring tube unit. The tampon may be 50 mm long, so that the portion near the withdrawal end of the tampon fits within the ring tube unit, thereby leaving about 30 mm of the insertion end of the tampon exposed. The film cap material may comprise, for instance, an approximately 38 micron stretchable LDPE planar film which is shaped into the film cap. To form the film cap, the planar film may be held under tension and drawn down over the top of the tampon, which is partially housed in the ring tube unit. It may then be stretched further down the sides of the ring tube unit where its ends are attached (e.g. with adhesive or a heat seal utilizing thermoplastic materials) to the ring tube unit such that it does not separate from the ring tube unit under normal usage conditions. Optionally, lines of weakness, in this case perforations, may be created in the film cap such that they break during expulsion of the tampon from the applicator.

In some cases, when more detailed conformability of the film sheath to the tampon is preferred, a heat-shrink film, which is optionally translucent, can be shrunk to the exposed portion of the tampon. For example a polyolefinic heat-shrink film is formed into a rectangular bag that is sufficiently large to easily slip the bag over the top of the exposed tampon down the side and over at least a portion of the ring tube unit. The bag is typically open only on the one end to permit enclosure of the applicator/tampon assembly. If seams are present in the bag, it is preferred that the smoother side of the seam be oriented outward. Proper heat is then applied to the exterior of the bag, which causes it to shrink and conform to the surface details of the tampon and applicator ring tube. In some cases, the shrinkage is sufficient to attach the sheath to the applicator ring tube without additional attachment means. Then, as desired, excess film is trimmed and lines of weakness are added at the top and/or sides of the film sheath.

Alternative applicator structures which may have loose or conforming insertion ends may comprise a bag of film, paper or non-woven; or a flexi-resilient, partially deformable formed sleeve or barrel, such as made via thermoforming with thicker polyolefinic film or sheet (e.g. 0.008 inch polyethylene sheet).

III. Wrappers Useful with the Shaped Tampons of the Present Invention

The shaped tampons of the present invention can optionally employ wrappers which are tightly conforming to the outer surface of the tampon in order to visually show the consumer the tampons packaged therein. Tightly conforming wrappers are particularly useful when the shaped tampons are intended to be used digitally and therefore are not housed in an applicator prior to use. The wrappers should substantially enclose each individual tampon and are intended to be removed prior to insertion and use. "Tightly conforming" means that there is substantially no visually noticeable void space between the wrapper and the tampon. In other words, the perimeter of the tightly conforming wrapper does not exceed the perimeter of the outer surface of the tampon by more than about 50%, alternatively not more than about 30%. In yet another embodiment, the wrapper on average does not exceed the perimeter more than about 10% or even not more than about 5%. Since the perimeter of a tampon typically changes as a function of the length of said tampon, especially because the tampon is shaped as described herein, the aforementioned limits for the tight conformation of the wrapper apply to at least all substantially lengthwise portions of the outer surface of the tampon, and preferably to all portions of the outer surface of the tampon. In some embodiments of the present invention some regions of the wrapper material may provide additional functional benefits, such as cord deployment means. In these regions the wrapper material may not tightly conform to the outer surface of the tampon along the entire length, but will still tightly conform to at least 70% of the lengthwise portions of the outer surface of the tampon described above. Alternatively, the wrappers of the present invention may tightly conform to at least 80% or even at least 90% of the lengthwise portions of the outer surface of the tampon. As an example, the aforementioned perimeters of the wrapper and the tampon can be measured along the length of the tampon in intervals of every 10% of the length of the tampon, excluding the ends of the wrapped tampon. Since tampons are typically made by compressing fibrous absorbent material into a self-sustaining shape, the tightly conforming wrapper can optionally be used to act with a certain compressing force on the outer surface of the tampon, which will aid maintaining said self-sustaining shape, in particular in the regions having smaller perimeters, by counteracting the expansion of the compressed material which otherwise would cause the perimeter of a portion of the shaped tampon to unduly grow during the normal steps prior to use (such as storage time within a retail package prior to purchase) to an undesirably larger perimeter. Depending on the circumstances and intended use, an undesirable growth in perimeter may range from about 5% to about 50%, or alternatively 10% to about 30% growth in perimeter.

Wrappers can be made to be tightly conforming through use of a variety of known techniques and/or materials. The wrapper material used can be any material suitable to be used for hygienically wrapping tampons. Suitable wrapper materials for use herein include flexible polymeric films, having a thickness of less than 1 mm. Examples for wrapper materials suitable for use with the present invention are polymeric films made of polyethylene, polypropylene, polyester, polystyrene, cellophane, polyamide, poly(vinyl chloride), ethylene-vinyl acetate copolymer and the like. Polyolefin materials such as polyethylene and polypropylene, or poly(vinyl chloride) are particularly useful as heat shrinkable materials and can be so used by one of ordinary skill in the art to form tightly conforming wrappers, typically utilizing heat seals to close off the wrapper edges. "Heat-shrinkable" as used herein refers to materials, which have an extension typically in at least two dimensions, e.g. films or nonwovens, and which reduce their extension in at least one of said dimensions when being heated to an elevated temperature above normal storage or usage temperatures, but being lower than their melting temperature or being lower than their decomposition temperature in case the material decomposes prior to melting.

Other techniques and/or materials can also be used to form the tightly conforming wrappers of the present invention. For instance, polyolefins and poly(vinyl chloride), can also be used as stretch films and heat seals used to close off the wrapper edges. Polystyrene and PET (polyethylenetherephthalate) are also useful, but since they are not heat sealable, an adhesive, for example, may be used to close off the wrapper. Alternatively, pre-stretched elastic materials can be formed from synthetic or natural (e.g. rubber) elastomers. Other embodiments include generally occlusive materials such as metallic foils (e.g. aluminum foil) which can be compressed manually to become tightly conforming wrappers. Non-occlusive or porous materials can also be used, such as nonwovens, wovens, scrims, meshes and papers to the degree that a tightly-conforming wrapper can be produced via stretching elastic type material or shrinking as described above. Such non-occlusive materials can be made occlusive by lamination with or by coating with occlusive material. In the case of cellulosic papers, examples include lamination with a polymeric film such as a polyolefinic composition, or coating or impregnation of the paper with wax. The aforementioned materials can also be coated with various chemical compounds to improve their barrier properties or the ability for sealing. Typically, the materials most suitable for use as wrapper materials with the present invention are heat-sealable for forming the wrapper by closing the wrapper material after having wrapped the tampon. Alternatives for closing the wrapper material are gluing, embossing, crimping, sewing, stitching, entangling, mechanical interlocking, cold pressure welding, or ultrasonic bonding.

Wrappers useful in the present invention may be provided with an opening means comprising at least one line of weakness. This opening means may further be able to prevent separation of the wrapper into more than one piece of wrapper material upon opening of the wrapper. For instance, the line of weakness may only extend around a portion of the wrapped tampon in terms of length and perimeter in order to prevent tearing-off of parts of the wrapper upon opening of the wrapper, which would result in fragmentation of the wrapper.

Generally, the wrapper of the present invention, in its most generic form, can be made by wrapping wrapper material around the tampon and sealing it onto itself for closing the wrapper material in order to substantially enclose the tampon. The sealing may be facilitated by pressure and optionally heat. In another embodiment of the invention a sleeve of the wrapper film material is formed and connected with an adhesive in an overlapping region. The sleeve can be put over the tampon and then heat shrunk. If needed, the end of the wrapper being assigned to the withdrawal and/or the insertion end of the tampon could be closed with an adhesive in order to form a pouch that is heat shrunk in the next step. When heat-shrinkable material is used, it can be shrunk after being closed around the tampon, decreasing the dimensions of the wrapper material so that the wrapper tightly conforms to the outer surface of the tampon. The same can be achieved by using stretch films, or even pre-stretched elastic material, which is allowed to relax into a non- or low-tensed or non- or low-stretched state after being closed around the tampon. Another alternative for achieving a tightly conforming wrapper is partially closing the wrapper after having wrapped the wrapper material around the tampon, then evacuating the interior of the wrapper by application of vacuum and finally completely closing the wrapper.

IV. Making the Tampon of the Present Invention

A method useful in making the tampons of the present invention involves the following steps: providing a first split cavity mold member having a first inner surface and a first outer surface; providing a second split cavity mold member having a second inner surface and a second outer surface; facing the first inner surface of the first split cavity mold member towards the second inner surface of the second split cavity mold member which results in a split cavity mold having a first end, a second end, and an opening located in the second end; providing an outer sleeve wherein the outer sleeve has a first end, a second end, and an opening located in the second end; inserting the first end of the split cavity mold into the outer sleeve, wherein the opening in the split cavity mold is visible through the second end of the outer sleeve and the outer sleeve holds together the first split cavity mold member and the second split cavity mold member and wherein the combination of the split cavity mold and the outer sleeve forms a joined sleeve cavity mold with a transfer end; loading the joined sleeve cavity mold into a v-block holder of a tampon compression machine with the transfer end of the joined sleeve cavity mold facing a compression jaw in the tampon compression machine; providing a tampon pledget; placing the tampon pledget into the compression jaw; actuating the compression jaw thereby compressing the tampon pledget into a high aspect ratio shape resulting in a compressed tampon pledget; transferring the compressed tampon pledget from an actuated jaw into the transfer end of the joined sleeve cavity mold using a compression member resulting in a tampon mold having a first end and a second end wherein the second end has an opening; removing the compression member from the opening of the tampon mold; removing the tampon mold from the tampon compression machine; self-sustaining the shaped tampon; and removing the shaped tampon from the tampon mold.

If microwaving is used as a self-sustaining method, the tampon mold is placed in a microwaving unit where the mold and the sleeve (if used) are made from a microwave-transparent material(s). After the tampon is self-sustained, the shaped tampon may be removed by removing the tampon mold from the microwaving unit. Then, the split cavity mold may be ejected from the outer sleeve through the second end of the outer sleeve. Next, the split cavity mold is split, that is at least partially separated or separated to the desired degree (e.g. partially opened) to aid the next step of tampon removal. Finally, the shaped tampon is removed from the split cavity mold.

It will be recognized by those of skill in the art that compression to a self sustaining form requires imparting both heat and pressure to the tampon pledget. Such heat and pressure cause the fibers to "set" and achieve this self-sustaining form subject to fluid expansion. Details of the above described method as well as other methods which may be used to form the tampons present invention are found in co-pending case Ser. No. 60/365,669, filed March 18, entitled "Method of Producing a Shaped Tampon", to "Sageser, et al.".

EXAMPLES

The following are a listing of examples illustrating various embodiments of the present invention. It would be obvious to those skilled in the art that various other changes and modifications can be made without departing from the spirit and scope of the invention.

Examples 1–7 provided below were tampons designed to have an absorbent capacity as measured by the standard syngyna test of between about 9 to about 12 grams. One of ordinary skill in the art will readily recognize that other absorbencies and sizes can be scaled up or down as desired. The total length of the tampons in the examples is 48 mm. The "Tampon Length" column below indicates the position on the tampon the perimeter measurements were taken relative to the total length of the tampon. The perimeter measurement at 0 mm is the withdrawal edge, the perimeter measurement at 48 mm is the insertion edge, the measurements listed in between fall sequentially along the X axis then, from withdrawal edge to insertion edge.

| Tampon length [mm] | Example 1 Perimeter [mm] | Example 2 Perimeter [mm] | Example 3 Perimeter [mm] | Example 4 Perimeter [mm] | Example 5[1] Perimeter [mm] | Example 6 Perimeter [mm] |
|---|---|---|---|---|---|---|
| 0 | 39.3 | 39.3 | 39.3 | 40.8 | 40.8 | 39.3 |
| 5 | 37.7 | 39.6 | 38.6 | 40.5 | 40.5 | 39.9 |
| 10 | 36.8 | 39.9 | 37.7 | 39.6 | 39.9 | 40.8 |
| 12 | 36.1 | 40.8 | 38.6 | 39.3 | 39.3 | 39.3 |
| 15 | 35.2 | 44.0 | 39.6 | 38.6 | 39.9 | 39.9 |
| 20 | 34.6 | 45.6 | 40.8 | 38.0 | 40.8 | 40.8 |
| 24 | 35.2 | 46.2 | 39.6 | 37.9 | 39.3 | 39.3 |
| 25 | 35.8 | 47.1 | 39.3 | 37.7 | 39.3 | 39.3 |
| 30 | 37.0 | 46.2 | 37.7 | 39.9 | 37.7 | 37.7 |
| 35 | 37.7 | 45.6 | 39.0 | 40.8 | 38.6 | 38.6 |
| 36 | 38.0 | 42.4 | 39.3 | 40.6 | 39.3 | 39.3 |
| 40 | 40.8 | 37.7 | 40.8 | 34.6 | 31.4 | 22.0 |
| 45 | 34.6 | 22.0 | 41.4 | 15.7 | 15.7 | 22.0 |
| 48 | 0 | 0 | 0 | 0 | 0 | 0 |

[1]This Example has 4 inflection points.

Example 7

A tampon is formed having a smallest withdrawal end perimeter of 39.3 mm, a largest insertion end perimeter of 40.8 mm, and a perimeter of less than 39.3 mm, for instance 37.9, in the center region.

Example 8

A tampon is formed having at least one center region perimeter of 37.7 mm and a largest insertion end perimeter of 40.8 mm. Thus, the center region has a perimeter which is 7.69% less than the largest insertion end perimeter.

Example 9

A tampon according to Example 4 is made wherein the withdrawal end is asymmetric.

Example 10

A tampon is made wherein the largest perimeter is located in the center region and is 41 mm.

Example 11

A tampon according to Example 4 is made wherein the average fiber density of the maximum perimeter region is 0.03960 g/cc and the average fiber density of the minimum perimeter region is 0.04650 g/cc. Thus, the average fiber density of the minimum perimeter region is 117% of the average fiber density of the maximum perimeter region.

Example 12

A tampon resembling FIG. 4 is made from a chevron shaped pledget wherein the volume of 5 mm sections, beginning at the withdrawal end and ending at the insertion end are as follows: 683.70 mm$^3$, 603.50 mm$^3$, 452.64 mm$^3$, 452.62 mm$^3$, 905.25 mm$^3$, 792.40 mm$^3$, 792.60 mm$^3$, 141.37 mm$^3$, 34.34 mm$^3$. For greater accuracy, volume measurements providing a greater number significant digits can be taken.

All documents cited are, in relevant part, incorporated herein by reference; the citation of any document is not to be construed as an admission that it is prior art with respect to the present invention.

What is claimed is:

1. A tampon comprising a mass of absorbent material form into a self-sustaining shape, said self-sustaining shape comprising: an insertion end, a withdrawal end, and a center region, wherein the insertion end is opposed to the withdrawal end and the center region is located between the insertion end and the withdrawal end; wherein said insertion end has a perimeter at the insertion edge and said withdrawal end has a perimeter at the withdrawal edge, said perimeter at said insertion edge being less than said perimeter at said withdrawal edge; wherein the self-sustaining shape has an outer surface which is substantially serpentine; and wherein the tampon has continually changing volume.

2. A tampon according to claim 1 wherein the insertion end is tapered and the withdrawal end is flared.

3. A tampon according to claim 2 wherein the withdrawal end is asymmetric about an X axis of the tampon.

4. A tampon according to claim 2 having a withdrawal edge which has a smaller perimeter than at least one withdrawal end perimeter.

5. A tampon according to claim 1 wherein the center region has at least one perimeter which is less than a largest insertion end perimeter.

6. A tampon according to claim 5 wherein the center region has at least one perimeter which is less than a withdrawal end perimeter.

7. A tampon according to claim 6 wherein at least one of the center region perimeters is from about 5% to about 25% smaller than a withdrawal end perimeter.

8. A tampon according to claim 5 wherein at least one of the center region perimeters is from about 10% to about 15% smaller than a largest insertion end perimeter.

9. A tampon according to claim 1 having a maximum perimeter region which has a maximum perimeter region average fiber density, and a minimum perimeter region which has a minimum perimeter region average fiber density; wherein the minimum perimeter region average fiber density is greater than the maximum perimeter region average fiber density.

10. A tampon according to claim 9 wherein the minimum perimeter region average fiber density is from about 105% to about 150% of the maximum perimeter region average fiber density.

11. A tampon according to claim 1 wherein the withdrawal end has a withdrawal end average fiber density, which is less than the minimum perimeter region average fiber density.

12. A tampon according to claim 11 wherein the minimum perimeter average fiber density is from about 105% to about 150% of the withdrawal end average fiber density.

13. A tampon according to claim 12 wherein a the maximum perimeter region and the withdrawal end comprise rayon having a first average fiber density and the minimum perimeter region comprises a cotton/rayon blend having a second average fiber density which is greater than the first average fiber density.

14. A tampon according to claim 11 wherein the minimum perimeter region average fiber density is from about 110% to about 130% of a maximum perimeter region average fiber density and/or the withdrawal end average fiber density.

15. A tampon according to claim 1 further comprising texturing on the outer surface.

16. A tampon according to claim 1 wherein the center region has a perimeter which is greater than or equal to all other perimeters.

17. A tampon according to claim 1 housed in an applicator wherein the applicator is at least partially translucent, allowing at least a portion of the tampon to be visible to a user prior to use.

18. A tampon according to claim 1 housed in an applicator; wherein the applicator comprises an insertion end comprising flexible material; and wherein at least a portion of the flexible material conforms to at least a portion of the substantially serpentine outer surface of the tampon, enabling a user to observe at least a portion of the substantially serpentine outer surface of the tampon through the flexible material prior to expulsion of the tampon from the applicator.

19. A tampon according to claim 1 wrapped in a tightly conforming wrapper.

20. A tampon according to claim 19 wherein the tightly conforming wrapper aids in maintaining the self-sustaining shape prior to use.

* * * * *